(12) United States Patent
Umar

(10) Patent No.: US 12,150,666 B2
(45) Date of Patent: Nov. 26, 2024

(54) FLUID ADAPTER ASSEMBLY

(71) Applicant: Sanusi Umar, Manhattan Beach, CA (US)

(72) Inventor: Sanusi Umar, Manhattan Beach, CA (US)

( * ) Notice: Subject to any disclaimer, the term of this patent is extended or adjusted under 35 U.S.C. 154(b) by 463 days.

(21) Appl. No.: 17/674,587

(22) Filed: Feb. 17, 2022

(65) Prior Publication Data

US 2023/0346417 A1 Nov. 2, 2023

(51) Int. Cl.
*A61B 17/3205* (2006.01)
*A61B 17/00* (2006.01)

(52) U.S. Cl.
CPC ............ *A61B 17/32053* (2013.01); *A61B 2017/00486* (2013.01); *A61B 2017/00752* (2013.01); *A61B 2217/007* (2013.01)

(58) Field of Classification Search
CPC .... A61B 17/32053; A61B 2017/00486; A61B 2017/00752; A61B 2217/007
See application file for complete search history.

(56) References Cited

U.S. PATENT DOCUMENTS

| | | | | |
|---|---|---|---|---|
| 4,988,334 | A * | 1/1991 | Hornlein | A61M 1/86 601/2 |
| 11,109,887 | B2 * | 9/2021 | Knowlton | A61B 18/1477 |
| 2009/0018568 | A1 * | 1/2009 | Bacher | A61B 17/32002 606/170 |
| 2011/0098688 | A1 * | 4/2011 | Gigon | A61B 17/32002 606/1 |
| 2019/0159793 | A1 * | 5/2019 | Cotter | A61M 3/0279 |

* cited by examiner

*Primary Examiner* — Mohamed G Gabr
*Assistant Examiner* — Andrew P. Restaino
(74) *Attorney, Agent, or Firm* — Bauer & Joseph

(57) ABSTRACT

An adapter assembly is configured to provide a fluid flow path for a rotary tool having a punch. The adapter assembly has a housing removably coupled to the rotary tool. the rotary tool has a lower end near a tip and an upper end away from the tip. A gasket is detachably arranged within the housing, around the punch and further comprising an upper seal portion and a lower seal portion. The upper seal portion has a smaller inner diameter than the lower seal portion. A fluid path is arranged through the housing, at least one hole in the gasket, and out of a lumen in the punch.

8 Claims, 4 Drawing Sheets

FLUID ADAPTER ASSEMBLY

BACKGROUND

This invention relates to surgical instruments and, more particularly, to a punch for extracting hair follicles from the skin.

Hair transplantation is a surgical technique that involves moving skin containing hair follicles from one part of the body (the donor site) to bald or balding parts (the recipient site).

Hair naturally grows in follicles that contain groupings of 1 to 4 hairs, and transplant techniques typically move the 1-4 hair "follicular units" from the donor site to the recipient site.

The follicles of hair are typically removed from the donor site using punches of between 0.7 mm and 1.25 mm in diameter. The punches are tubular bodies having a skin-contacting cutting edge, and are typically mounted in a tool that causes the punch to rotate as the punch is brought into contact with the donor site. Hair follicles are very easily damage during the removal process, and damaged follicles are unlikely to be successfully transplanted.

One way that punches can be made more effective is by introducing fluid into the donor site, but this raises a new set of problems. Fluid has a tendency to corrode metallic systems, in particular the motor and moving parts of a punch are susceptible to corrosion and failure. What is needed is a fluid adapter that ensures fluid is localized to the donor site and stopped from the moving parts of the punch.

SUMMARY

An adapter assembly is configured to provide a fluid flow path for a rotary tool having a punch. The adapter assembly has a housing removably coupled to the rotary tool. the rotary tool has a lower end near a tip and an upper end away from the tip. A gasket is detachably arranged within the housing, around the punch and further comprising an upper seal portion and a lower seal portion. The upper seal portion has a smaller inner diameter than the lower seal portion. A fluid path is arranged through the housing, at least one hole in the gasket, and out of a lumen in the punch.

In some instances, an obstruction in the lumen is pushed out of the lumen by the fluid traveling in the fluid flow path In some instances, a recalcitrant obstruction in the lumen causes the fluid to travel to the gasket, around the punch and out of the housing.

In some embodiments, there is at least on hole in the housing. A recalcitrant obstruction in the lumen can causes the fluid to travel to the gasket, around the gasket and out of the at least one hole in the housing.

In some embodiments, the housing further comprises an upper groove mated to the upper seal portion and a lower protrusion mated to the lower seal portion.

In some embodiments, the punch has a fluid opening, an upper circumferential indent, and a lower circumferential indent. The fluid opening is aligned with the at least one hole in the gasket. The upper circumferential indent is aligned with an upper notch inside of the gasket. The lower circumferential indent is aligned with the lower notch inside of the gasket.

In some embodiments, an installer is arranged against the gasket to mount the gasket into the housing.

In some embodiments, an upper seal portion inner diameter is at least 50 microns but no more than 400 microns smaller than a lower seal portion inner diameter.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
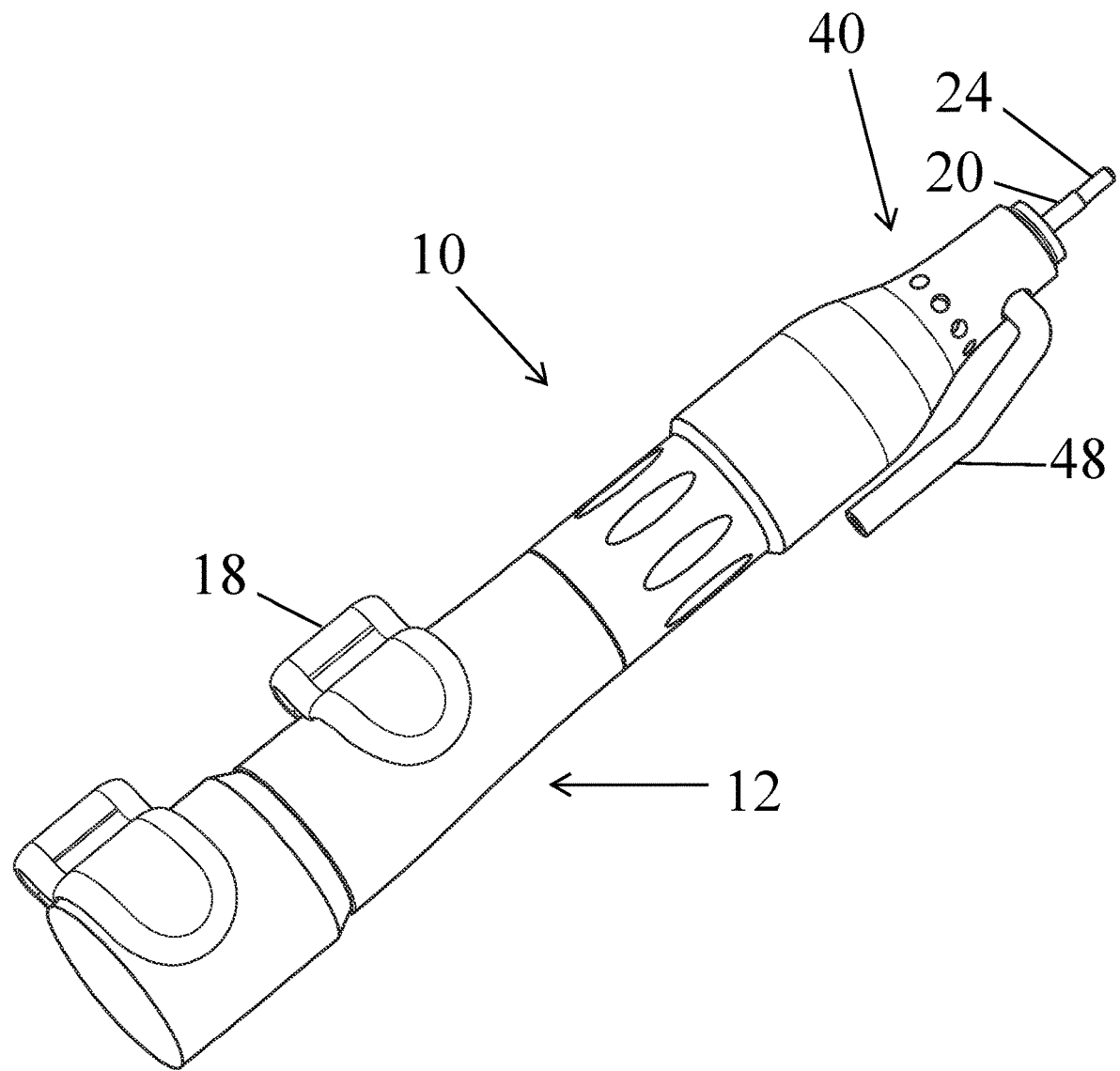
FIG. 1 shows a perspective view of one embodiment of the present invention.
Figure 2:
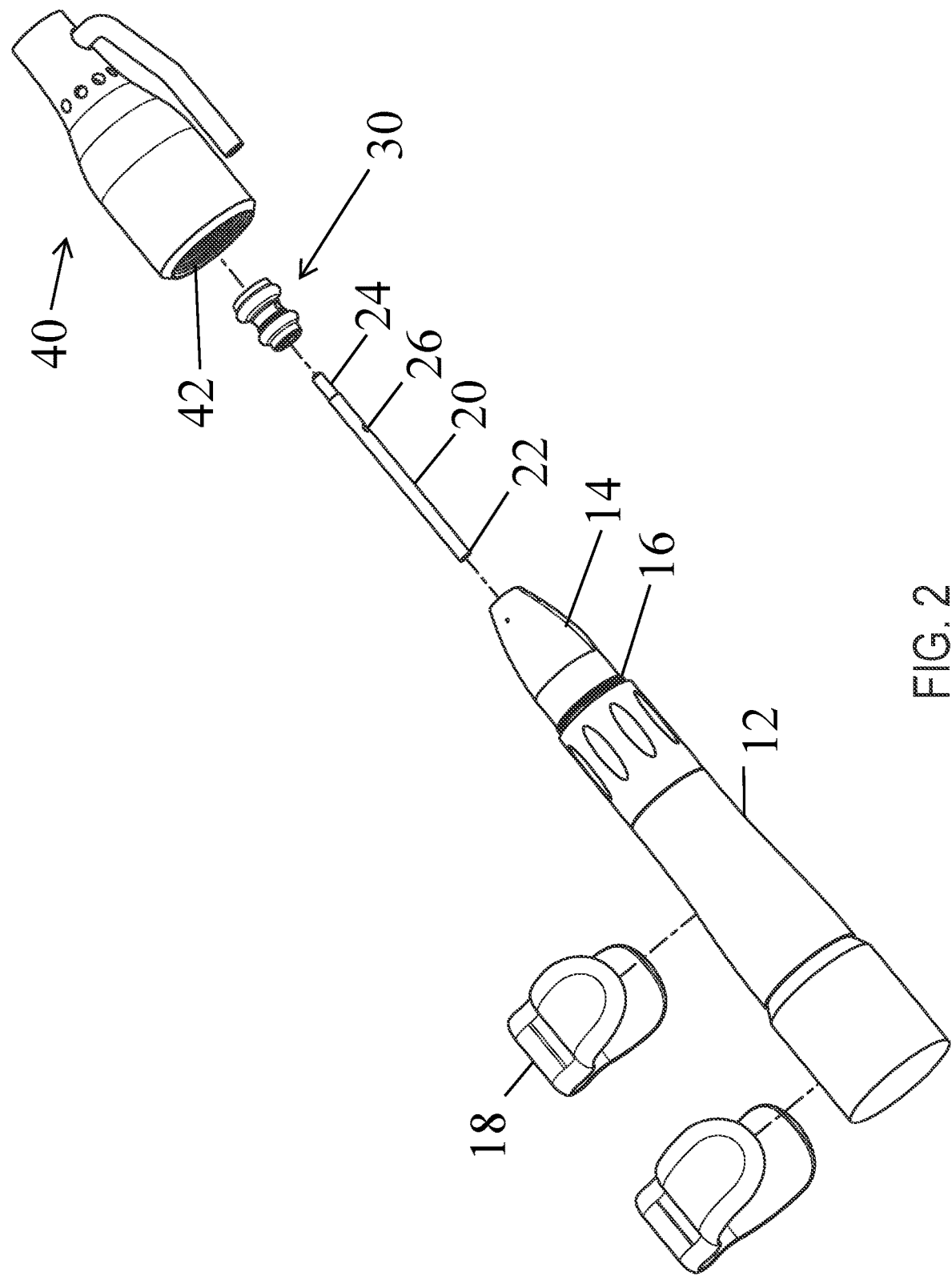
FIG. 2 shows an exploded view of one embodiment of the present invention.
Figure 3:
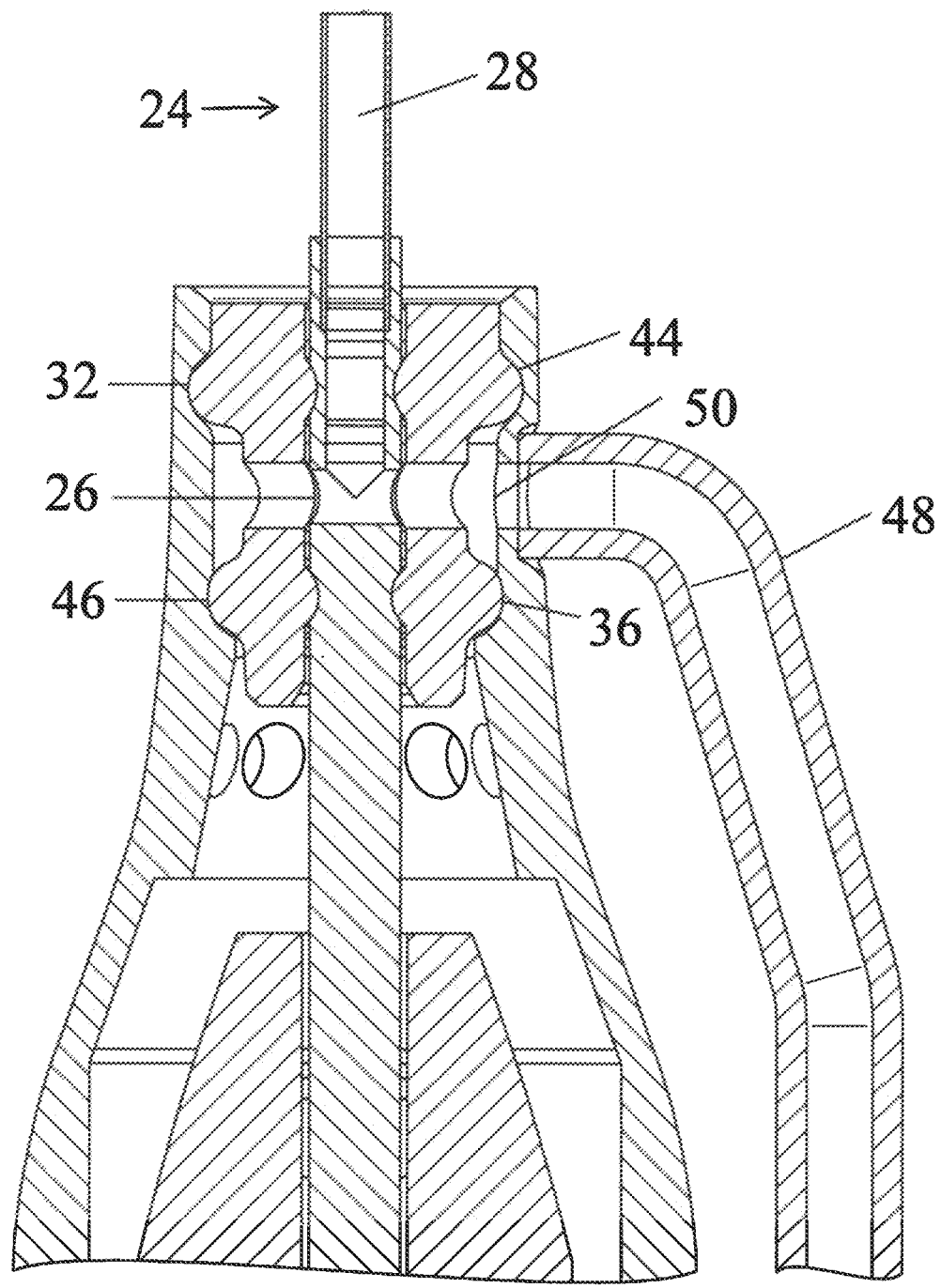
FIG. 3 shows a section view of one embodiment of the present invention taken along line 3-3 in FIG. 1.
Figure 4:
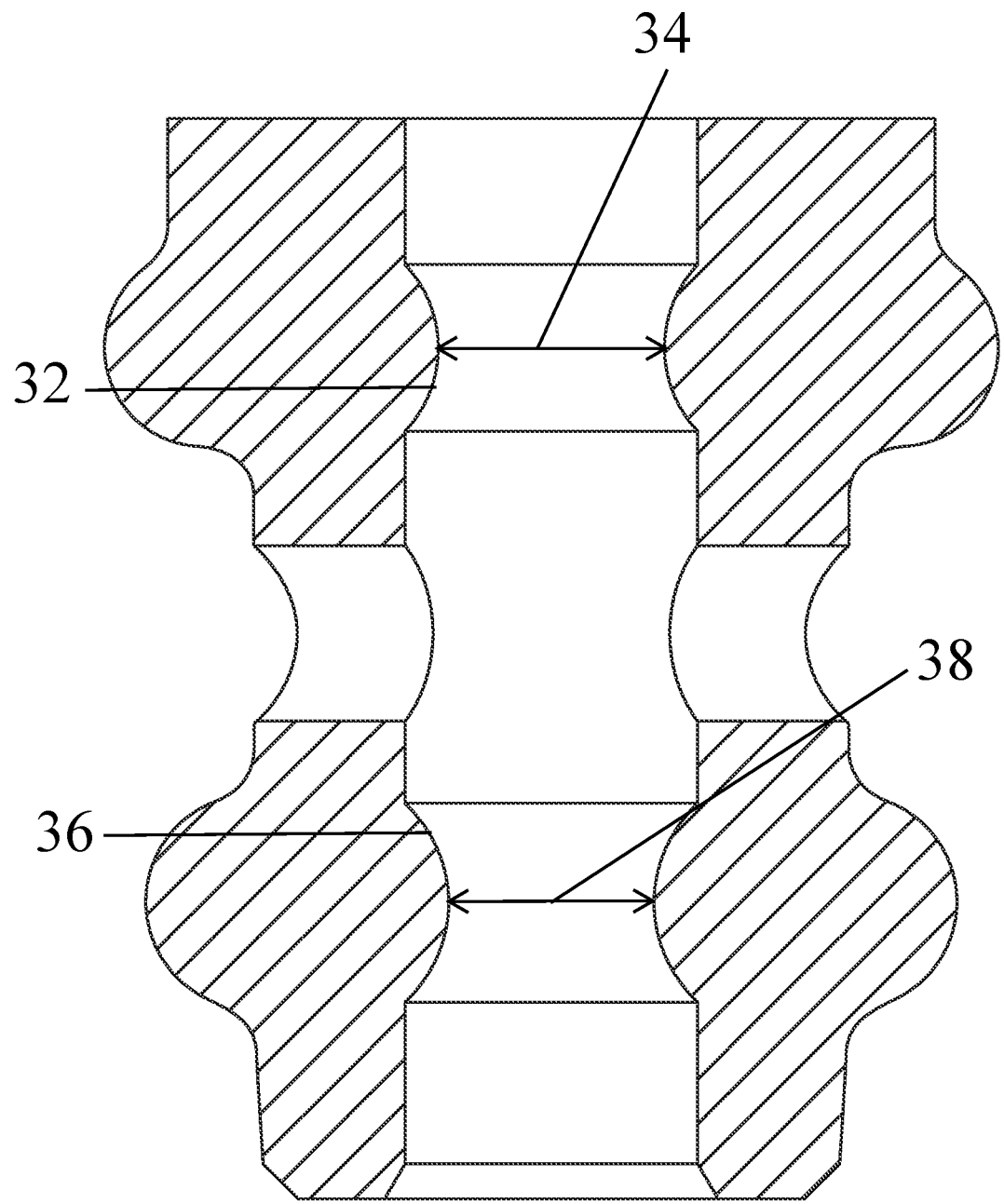
FIG. 4 shows a section view of one embodiment of the present invention taken along line 4-4 in FIG. 2.

By way of example, and referring to FIGS. 1-2, one embodiment of an adapter assembly 10 further comprises a rotary tool 12 joined to a punch 20. A gasket 30 slides over the punch 20. A fluid adapter 40 fits over the punch 20 and the gasket 30 and is attached to the rotary tool 12.

The rotary tool 12 further comprises a chuck 14 that is attached to the punch 20. The rotary tool 12 further comprises external threads 16 and can be attached to clips 18.

The punch 20 further comprises a chuck end 22 that is inserted into the chuck 14. The punch 20 further comprises a contact end 24, opposite the chuck end 22 which is configured to contact the skin of a patient. Between the chuck end 22 and the contact end 24 is a at least one punch fluid opening 26. The punch 20 has a hollow portion 28 extending from the at least one punch fluid opening 26 to the contact end 24.

The gasket 30 is detachably arranged within the fluid adapter 40, around the punch 20. The gasket 30 further comprising an upper seal portion 32 that has an upper seal portion inner diameter 34 and a lower seal portion 36 that has a lower seal portion inner diameter 38. The upper seal portion inner diameter 34 is less than the lower seal portion inner diameter 38. In some embodiments, the upper seal portion inner diameter 34 is at least 50 microns but no more than 400 microns smaller than the lower seal portion inner diameter 38.

The fluid adapter 40 further comprises fluid adapter internal threads 42, a fluid adapter upper groove 44, a fluid adapter lower groove 46, and a fluid adapter fluid source tube 48. The fluid adapter internal threads 42 are mated with the external threads 16 to join the fluid adapter to the rotary tool. The fluid adapter upper groove 44 accommodates the upper seal portion 32. The fluid adapter lower groove 46 accommodates the lower seal portion 36.

When so aligned the fluid adapter fluid source tube 48 is aligned with a gasket opening 50 on the gasket 30 and the at least one punch fluid opening 26. This creates a fluid path allowing fluid to travel from a fluid source and out of a lumen at the contact end 24.

In some instances, an obstruction in the lumen is pushed out of the lumen by the fluid traveling through the fluid path. In some instances, a recalcitrant obstruction in the lumen causes the fluid to travel to the gasket 30, around the punch 20 and out of the fluid adapter 40.

In some embodiments, there is at least on hole in the fluid adapter 40. A recalcitrant obstruction in the lumen can causes the fluid to travel to the gasket 30, around the gasket 30 and out of the at least one hole in the fluid adapter 40.

As used in this application, the term "a" or "an" means "at least one" or "one or more."

As used in this application, the term "about" or "approximately" refers to a range of values within plus or minus 10% of the specified number.

As used in this application, the term "substantially" means that the actual value is within about 10% of the actual desired value, particularly within about 5% of the actual desired value and especially within about 1% of the actual desired value of any variable, element or limit set forth herein.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. An adapter assembly, configured to provide a fluid flow path for a rotary tool having a punch; the adapter assembly comprising:
   a housing, removably coupled to the rotary tool; the rotary tool having a lower end near a tip and an upper end away from the tip;
   a gasket detachably arranged within the housing, around the punch and further comprising an upper seal portion and a lower seal portion;
   wherein the upper seal portion has a smaller inner diameter than the lower seal portion; and
   the fluid flow path, arranged through the housing, through at least one hole in the gasket, and out of a lumen in the punch.

2. The adapter assembly of claim 1, wherein an obstruction in the lumen is pushed out of the lumen by fluid traveling in the fluid flow path.

3. The adapter assembly of claim 1, wherein a recalcitrant obstruction in the lumen causes fluid traveling in the fluid flow path to travel to the gasket, around the punch, and out of the housing.

4. The adapter assembly of claim 1, further comprising, and at least one hole in the housing; wherein a recalcitrant obstruction in the lumen causes fluid traveling in the fluid flow path to travel to the gasket, around the gasket, and out of the at least one hole in the housing.

5. The adapter assembly of claim 4, wherein the housing further comprises an upper groove mated to the upper seal portion and a lower protrusion mated to the lower seal portion.

6. The adapter assembly of claim 5, further comprising the punch having a fluid opening, an upper circumferential indent, and a lower circumferential indent
   wherein the fluid opening is aligned with the at least one hole in the gasket;
   wherein the upper circumferential indent is aligned with an upper notch inside of the gasket;
   wherein the lower circumferential indent is aligned with a lower notch inside of the gasket.

7. The adapter assembly of claim 1, further comprising an installer, arranged against the gasket to mount the gasket into the housing.

8. The adapter assembly of claim 1, wherein the upper seal portion inner diameter is at least 50 microns but no more than 400 microns smaller than the lower seal portion inner diameter.

* * * * *